(12) United States Patent
Fuchs et al.

(10) Patent No.: US 7,182,474 B2
(45) Date of Patent: Feb. 27, 2007

(54) HOLDING DEVICE HAVING A TRANSPARENT COVER ELEMENT FOR A DRAPE

(75) Inventors: Holger Fuchs, Aalen (DE); Ottmar Rothaupt, Aalen (DE)

(73) Assignee: Carl-Zeiss-Stiftung, Oberkochen (DE)

( * ) Notice: Subject to any disclaimer, the term of this patent is extended or adjusted under 35 U.S.C. 154(b) by 0 days.

(21) Appl. No.: 10/772,335

(22) Filed: Feb. 6, 2004

(65) Prior Publication Data
US 2004/0156100 A1    Aug. 12, 2004

(30) Foreign Application Priority Data
Feb. 6, 2003    (DE) ................. 103 04 967
Mar. 14, 2003    (DE) ................. 103 11 198

(51) Int. Cl.
*G02B 21/00*    (2006.01)
(52) U.S. Cl. ...................................... 359/510
(58) Field of Classification Search ................ 359/507, 359/510, 511; 600/121, 125
See application file for complete search history.

(56) References Cited

U.S. PATENT DOCUMENTS

| | | | |
|---|---|---|---|
| 3,528,720 A | * | 9/1970 | Treace ......................... 359/510 |
| 3,698,791 A | * | 10/1972 | Waichle et al. ............. 359/510 |
| 5,467,223 A | | 11/1995 | Cleveland, Jr. et al. |
| 5,608,574 A | | 3/1997 | Heinrich |
| 6,024,454 A | | 2/2000 | Horan et al. |
| 6,257,730 B1 | | 7/2001 | Kleinberg et al. |
| 2005/0094269 A1 | * | 5/2005 | Moses et al. ................ 359/510 |

FOREIGN PATENT DOCUMENTS

DE    44 13 920    12/1994

* cited by examiner

*Primary Examiner*—Mark A. Robinson
(74) *Attorney, Agent, or Firm*—Walter Ottesen

(57) ABSTRACT

A drape (101) for a surgical microscope (100) is attached to the surgical microscope (100) with a holding device (103) in the region of the surgical microscope main objective (104). The holding device (103) can accommodate a cover element (105). A tongue-shaped section is provided on the holding device (103) which applies a spring force to an outer peripheral surface of the surgical microscope main objective (104) when the holding device is arranged on the surgical microscope main objective (104) so that the holding device is held force-tight and friction-tight on the surgical microscope main objective. The cover element (105) can be inserted laterally into the holding device (103).

62 Claims, 5 Drawing Sheets

HOLDING DEVICE HAVING A TRANSPARENT COVER ELEMENT FOR A DRAPE

CROSS REFERENCE TO RELATED APPLICATION

This application claims priority of German patent applications no. 103 04 967.3, filed Feb. 6, 2003, and 103 11 198.0, filed Mar. 14, 2003, the entire contents of which are incorporated herein by reference.

FIELD OF THE INVENTION

The invention relates to a holding device for attaching a drape for a surgical microscope in the region of the main objective of the surgical microscope. The holding device has a recess for the main objective. The invention also relates to at least a partially transparent cover element having a window section for the passage of an illuminating beam path and/or a viewing beam path in a surgical microscope with a holding section for holding the cover element in a holding device. Finally, the invention relates to a holding device having a cover element and a drape having such a holding device.

BACKGROUND OF THE INVENTION

Surgical microscopes are covered with a sterile protective covering in order to make possible sterile work with surgical microscopes in operating rooms. The protective covering is a so-called drape. Such protective coverings are available from Microtek Medical, Inc. under reference numeral 4865 CL or from the Pharma-Sept Ltd. under the reference numeral 80-266 SB.

These sterile protective coverings have a viewing opening for the surgical microscope main objective so that the view through the surgical microscope onto the operating area is not affected. This viewing opening is, as a rule, formed by a holding device which is enclosed and sealed by a circularly-shaped cutout of the sterile protective covering. The holding device is attached to the main objective of the surgical microscope and carries a protective element of glass or plastic which covers the main objective of the surgical microscope.

A holding device of the kind referred to above is disclosed, for example, in U.S. Pat. No. 5,608,574. There, a protective covering for a surgical microscope is described wherein a holding device in the form of an insert in the protective covering is provided. This insert has a radial flange extending outwardly. This flange is glued to the protective covering and is enclosed by an edge of a viewing opening. The flange has a circularly-shaped recess having several ribs at its inner wall which extend in a longitudinal direction. The inner diameter of the flange is adapted to the outer diameter of a surgical microscope main objective. The flange can be pushed onto a main objective of a surgical microscope in order to hold friction-tight on the outer wall of the main objective under the clamping action of the ribs. At its lower side, the holding device is cut at an angle and there has a receptacle for a transparent cover element which protects the surgical microscope main objective against contamination and makes possible also the sterile work with the surgical microscope.

The cover element is configured to be disc shaped. The cover element has projecting ribs which, with projections at the lower side of the holding device, make possible a connection of cover element and holding device. This connection has the form of a bayonet connection and can be opened and closed by turning the cover element relative to the holding device.

A holding device for a sterile protective covering on a surgical microscope main objective is described in U.S. Pat. No. 6,024,454 and this holding device includes an adapter ring which is pushed onto the main objective of the surgical microscope. A clamping screw is provided for adjusting the clamping force for the adapter ring mounted on the main objective of the surgical microscope. A spring biased O-ring is provided on the outer side of the adapter ring and a ring connected to the sterile protective covering is pushed onto this O-ring in order to provide a friction-tight hold. A cover glass can be attached by means of a bayonet connection at the lower side of the ring tightly connected to the sterile protective covering.

U.S. Pat. No. 6,257,730 discloses a sterile protective covering having a holding device for covering a surgical microscope with this holding device being made of elastomer. This holding device is placed about the main objective of the surgical microscope in order to hold the protective covering friction-tight or force-tight.

U.S. Pat. No. 5,467,223 discloses a sterile protective covering having a holding device for attaching to a main objective of a surgical microscope. The holding device includes an adapter unit which can be threadably engaged in a housing for the surgical microscope main objective. Furthermore, U.S. Pat. No. 5,467,223 discloses a holding device which includes an adapter unit which can be threadably mounted outside on a surgical microscope main objective. This adapter unit is configured to have an annular shape and preferably comprises a rigid material such as aluminum. In the holding device, a ring element made of elastomer material is provided which is tightly connected to the sterile protective covering. This ring element can be pushed over the adapter unit in order to hold the protective covering on the surgical microscope in the region of the main objective thereof.

SUMMARY OF THE INVENTION

It is an object of the invention to provide a holding device for attaching a protective covering for a surgical microscope in the region of the main objective thereof which can be pushed onto a surgical microscope main objective in a simple manner without additional adapter elements and which can be used for different objective diameters. It is a further object of the invention to make available a cover element for a surgical microscope with the cover element having a window section for passing an illuminating beam path and/or a viewing beam path. The cover element can be easily exchanged in such a holding device.

The holding device of the invention is for attaching a drape for a surgical microscope in the region of the main objective thereof. The main objective has an outer peripheral surface and the holding device includes: a holding unit defining a recess for the objective; and, the holding unit having a tongue-shaped section for applying a spring force onto the outer peripheral surface of the main objective when the holding unit is mounted on the main objective in order to force-tightly hold the holding unit on the main objective.

In this way, a holding device is provided which can be manufactured in a cost-effective manner and which is suitable for different types of surgical microscopes and can be manufactured from comparatively stiff or hard material which can be conveniently sterilized.

In a further embodiment, a plurality of tongue-shaped sections is provided. In this way, a holding device is provided which is self-centering when pushing the same onto a main objective of a surgical microscope and can be especially comfortably pushed onto the main objective because the holding device must not be introduced into a fit or frame.

In another embodiment of the invention, the holding device has an annularly-shaped section and the tongue-shaped sections extend in an inclined direction to an axis of the annularly-shaped section. In this way, a deformation can be minimized when bending the tongue-shaped sections.

In a further embodiment of the invention, the tongue-shaped sections are directed toward the inner side of the ring-shaped section. In this way, a flat configuration of the holding device is made possible.

In a further embodiment of the invention, the tongue-shaped sections have different lengths. In another embodiment of the invention, the direction of the tongue-shaped sections to the axis of the annularly-shaped section is different. In this way, a tight seating of the holding device is made possible on surgical microscopes having different objective diameters.

In a further embodiment of the invention, at least one stop element is provided in the holding device for stopping against an end face region of a main objective of a surgical microscope. In this way, a straight seating of the holding device on a main objective of a surgical microscope is made possible.

In a further embodiment of the invention, means for holding a cover element are formed on the holding device. In this way, the holding device can be combined with a cover element so that, during surgery, a surgical field can be held sterile and the main objective of the surgical microscope can be protected against contamination and also against damage.

In a further embodiment of the invention, the means for holding a cover element have a guide for the cover element. In this way, the cover element can be easily exchanged during surgery.

In a further embodiment of the invention, the means for holding the cover element can include clamping means. In this way, a tight seating of the cover element on the holding device is ensured.

In a further embodiment of the invention, the means for holding the cover element includes latching means.

In a further embodiment of the invention, the guide for the cover element includes a stop section. In this way, a pregiven seating for the cover element is easily adjustable.

In a further embodiment of the invention, the holding device is made of plastic, preferably, thermoplast. In this way, a holding device is produced in a cost-effective manner, for example, in an injection molding process.

For a cover element of the type mentioned initially herein, linear guide means are provided in the holding section for the lateral introduction of the cover element into a holding device. In this way, the cover element can be easily exchanged during surgery.

In a further embodiment of the invention, the holding section of the cover glass has at least partially a thickened edge. In this way, the cover element holding section withstands mechanical loading.

In a further embodiment of the cover element, at least one notch is formed in the thickened edge. In this way, a latch seat of the cover glass in the holding device is made possible.

A handle is provided in a further embodiment of the cover element. In this way, a cover element can be easily exchanged.

In a further embodiment, the region of the holding section, which lies opposite the handle includes a boundary edge having a convex contour. In this way, a cover element is provided which is self aligning when introduced into a correspondingly configured holding device.

In a further embodiment of the invention, the boundary edge of the cover element has rounded corner regions. In this way, it is ensured that a user of the surgical microscope does not get injured on the cover glass and, furthermore, the cover glass does not become jammed in the holding device.

In a further embodiment of the invention, a window base is provided which carries the window section. In this way, the window section of the cover element can be configured inclined to the optical axis of a surgical microscope main objective.

In a further embodiment, the window base of the cover element is configured with a conical cross section. In this way, an easy stacking of cover elements is made possible.

In a further embodiment of the invention, the window section is inclined to a holding section in the cover element. In this way, light reflections on the cover element from a surgical field illumination, which passes through the surgical microscope main objective, are minimized. These light reflections can otherwise be disturbing to the viewer.

Advantageously, the cover element is so matched to the holding device that it can be accommodated therein with two orientations rotated by 180° to each other.

The cover element can be especially cost effectively manufactured in that the cover element is made of transparent plastic, preferably, PMMA.

A holding device with such a cover element and a drape for a surgical microscope with a corresponding holding device makes possible a user-friendly complete sterile sheathing or covering of a surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
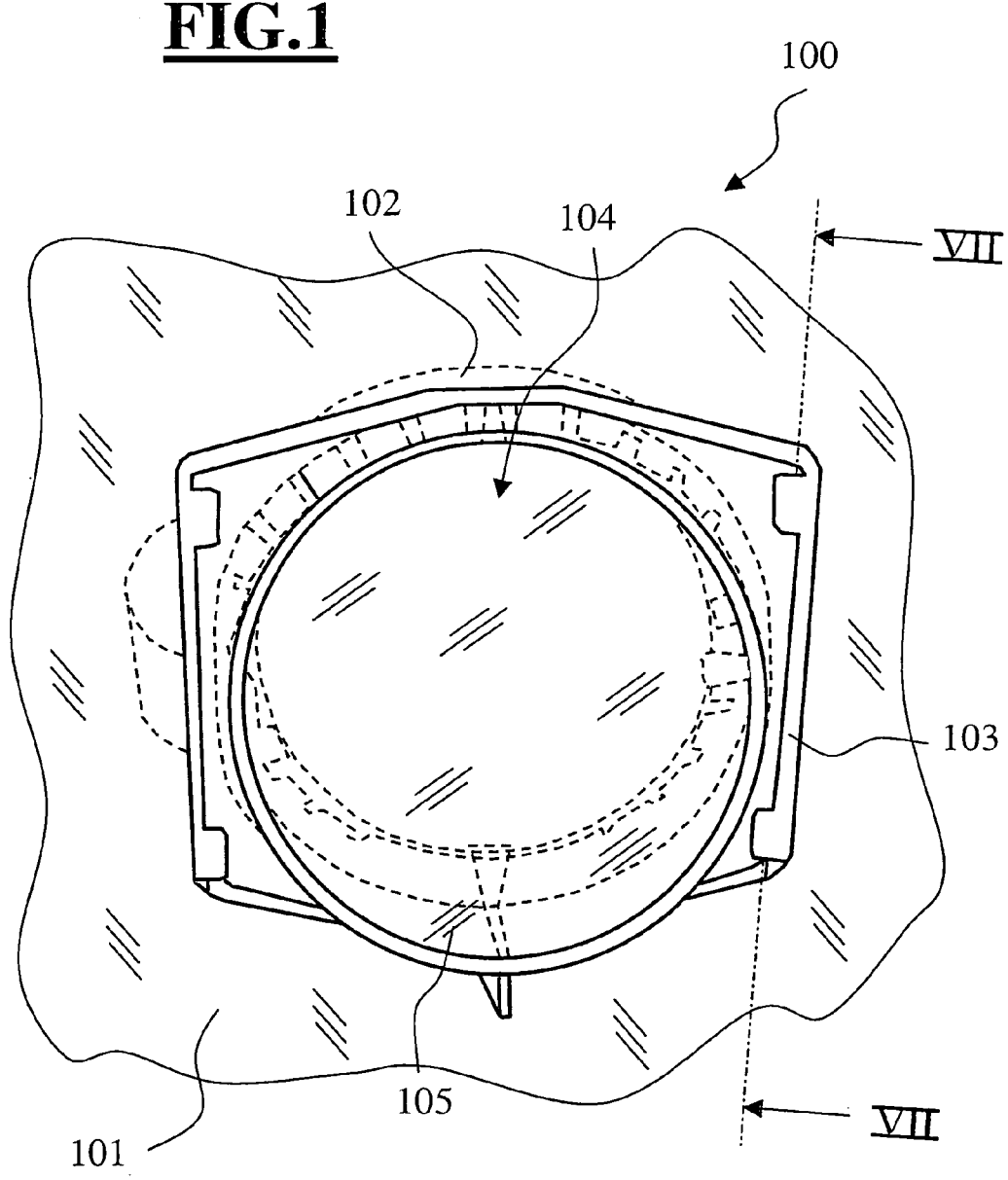
FIG. 1 is a section of a surgical microscope covered with a drape with the drape being attached to a surgical microscope main objective with a holding device wherein a cover element is inserted.

FIG. 1 shows a portion 100 of a surgical microscope which is surrounded by a protective covering 101. The protective covering 101 is attached to an outer flange 102 of a holding device 103. The holding device 103 preferably is made of thermoplastic plastic (for example, PE-LP) and is mounted on the main objective 104 of the surgical microscope 100. In the holding device 103, a cover element 105 is inserted which is preferably made of plastic, for example, PMMA. This cover element 105 protects the main objective 104 of the surgical microscope against contamination during surgery and ensures a sterile operating field for the protection of the patient.

Figure 2:
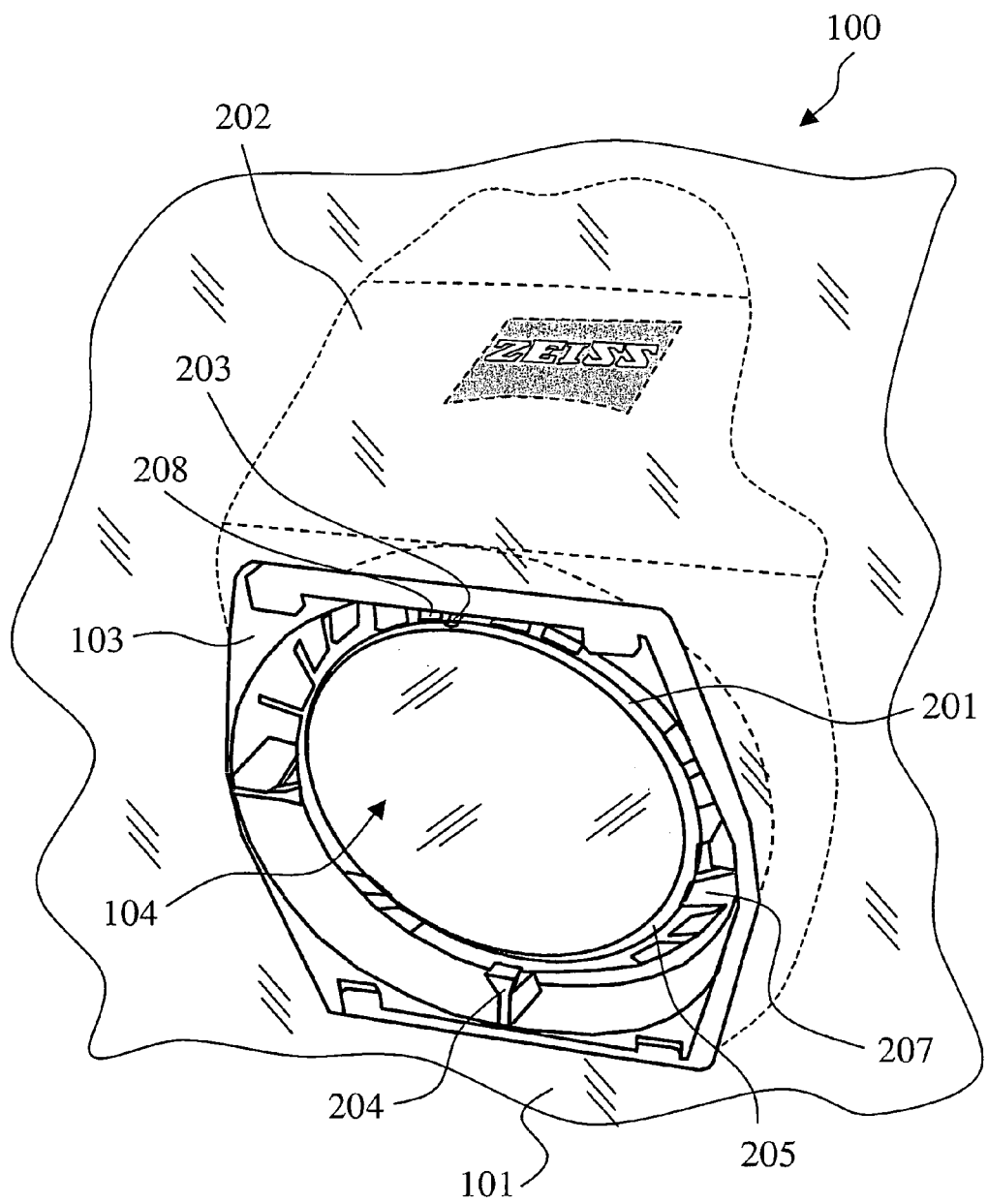
FIG. 2 is a perspective view of the surgical microscope with the drape and holding device but without the cover element.

FIG. 2 shows the surgical microscope portion 100 having a protective covering 101 and a holding device 103 without a cover element. Insofar as FIG. 2 shows the same components as FIG. 1, the same reference numerals are used hereinafter. The surgical microscope main objective 104 projects with a cylindrically-shaped surgical microscope main objective flange 201 from the base body 202 of the surgical microscope. The holding device 103 with a central recess 203 is pushed on this cylindrically-shaped surgical microscope main objective flange 201 up to stops 204 on an end face region 205 of the surgical microscope main objective flange 201. The protective covering 101 is held on the outer flange 102 of the holding device 103 preferably with a weld connection or an adhesive connection.

Tongue-shaped sections 207 and 208 are formed in a recess of the holding device and these sections 207 and 208 lie against the outer flange 201 of the surgical microscope main objective 104 and apply a spring force to this outer flange 201. This spring force acts with a perpendicular force component against the outer peripheral surface of the outer flange 201 and there effects a force-tight or friction-tight grip of the holding device 103.

Figure 3:
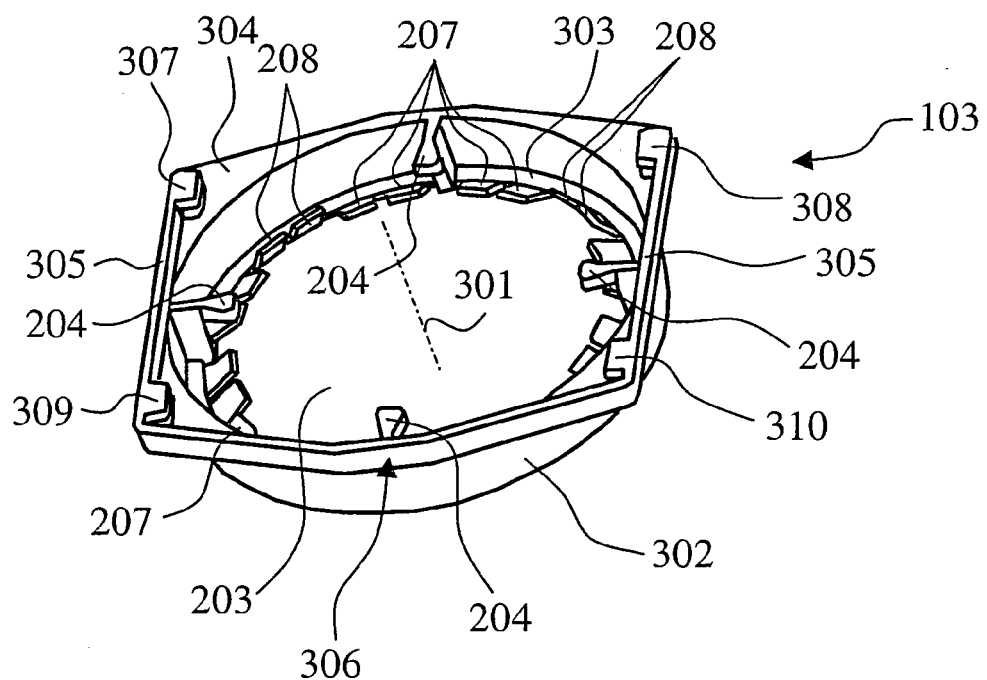
FIG. 3 is a perspective view of the holding device as seen from a first direction.
Figure 4:
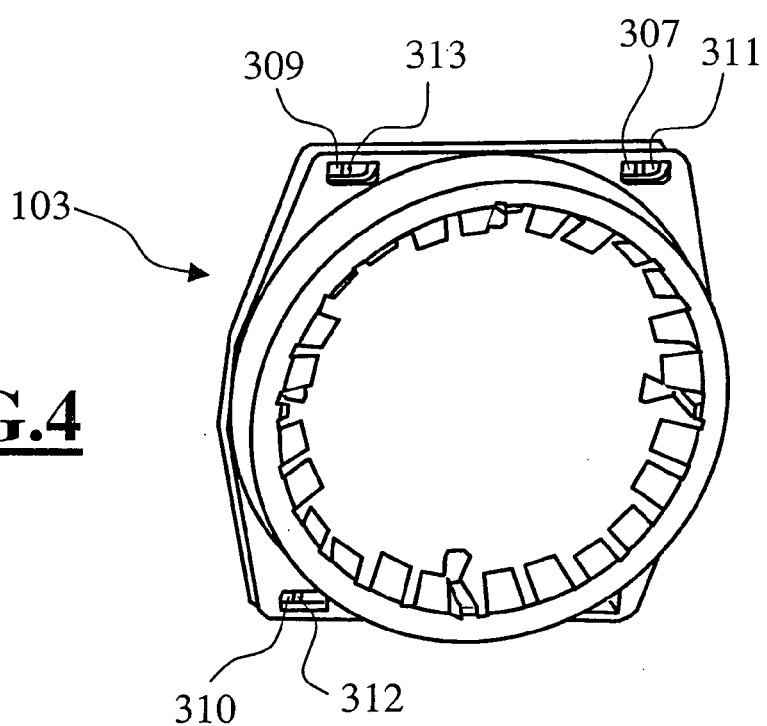
FIG. 4 is a perspective view of the holding device as seen from a second direction.

FIGS. 3 and 4 show a detail view of the holding device 103 of FIGS. 1 and 2. Insofar as sections of the holding device are identical, which have already been explained with respect to FIGS. 1 and 2, the same reference numerals are used hereinafter for their description. The holding device 103 has a recess 203 which is formed by an annularly-shaped side wall 302. The tongue-shaped sections 207 and 208 are formed on this annularly-shaped side wall 302. The sections 207 and 208 project from the side wall 302 inclined inwardly toward the recess 203. The annularly-shaped side wall 302 also has an edge 303 which is directed toward the surgical microscope when the holding device is pushed onto the surgical microscope main objective. The holding device 103 further has a joining region 304 which lies on the side facing away from the surgical microscope main objective when the holding device is pushed on. The tongue-shaped sections 207 and 208 are fixed in a collar-shaped region of the edge 303 pointing inwardly. With reference to an axis 301 of the recess 203, the tongue-shaped sections 208 are directed at a steeper angle into the center of the recess 203 than is the case for the tongue-shaped sections 207. Furthermore, the tongue-shaped sections 208 are configured to be shorter than the tongue-shaped sections 207. When mounting the holding device on the outer flange of a surgical microscope main objective, the tongue-shaped sections are bent for a corresponding objective diameter whereby the sections apply a perpendicular force component to the outer peripheral surface of the surgical microscope main objective. This perpendicular force component is caused by the spring force. When pushing the holding device onto a surgical microscope main objective, especially these different angles or the different directions of the tongue-shaped sections 207 and 208 make possible a force-tight and friction-tight seating of the holding device on the outer peripheral surface of the surgical microscope main objective over a certain region independently of the objective diameter of the main objective.

Furthermore, the form of the tongue-shaped sections 207 and 208 causes the holding device 103 to be self-centering when being pushed onto a surgical microscope main objective. As explained with respect to FIGS. 1 and 2, the pushed-on holding device then lies with stops 204 against the end face of the surgical microscope flange 201. This makes possible, in a simple manner, an even seating of the holding device 103 on the surgical microscope main objective with the holding device adjusting itself. If the holding device 103 is pushed onto the outer flange of a surgical microscope main objective, then the stops 204 lie against the end face of the surgical microscope main objective so that the seating of the holding device is stabilized and the holding device is protected against tilting.

The joining region 304 for the cover element includes an edge 305 having a stop section 306 on which longitudinal guiding brackets 307, 308, 309 and 310 are arranged. These longitudinal guiding brackets 307 to 310 form, in the manner of a drawer guide, a guide slot for a corresponding cover element. Breakthroughs lie opposite the longitudinal guiding brackets 307 to 310 which can correspond to dip cores of an injection mold. Such a holding device can be manufactured at low manufacturing costs in an injection molding process.

As shown in FIG. 4, the longitudinal guiding brackets 307 to 310 have an inclined flattened region 311 which facilitates the introduction of a cover glass. Detents 312 and 313 are held in the longitudinal guiding brackets 309 and 310. The outwardly directed corner and edge regions of the holding device are configured to be rounded in order to minimize a danger of injury for the user and especially to prevent the cutting open of the sterile gloves.

Figure 5:
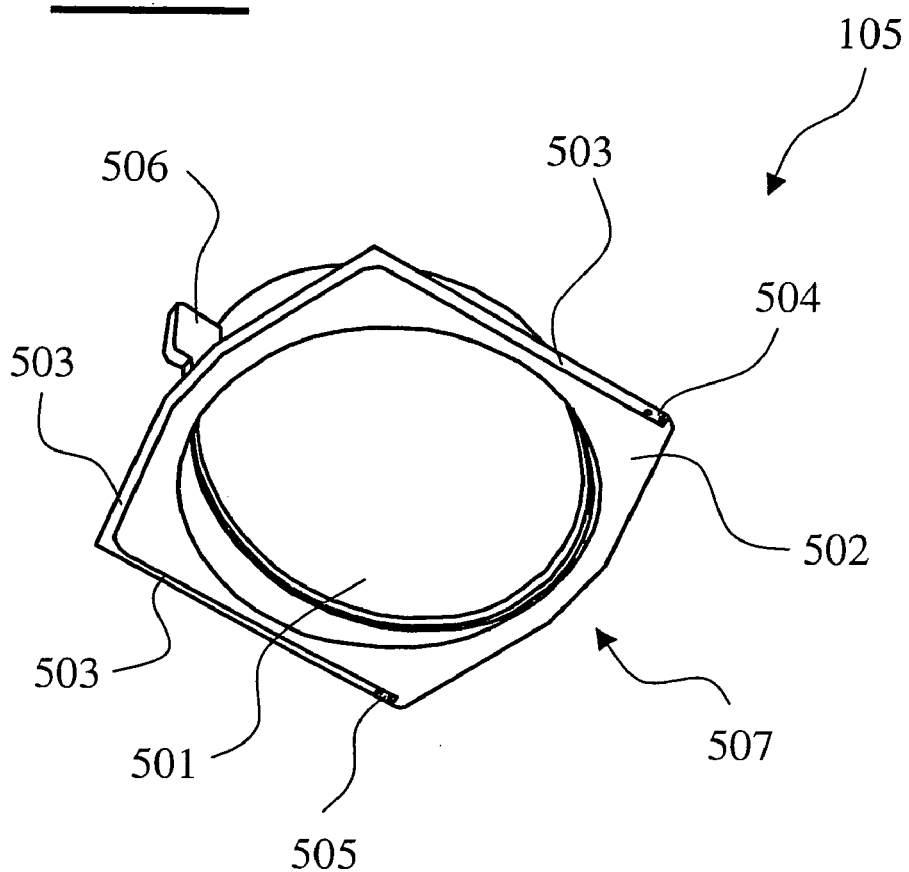
FIG. 5 is a perspective view of the cover element as seen in a first direction.
Figure 6:
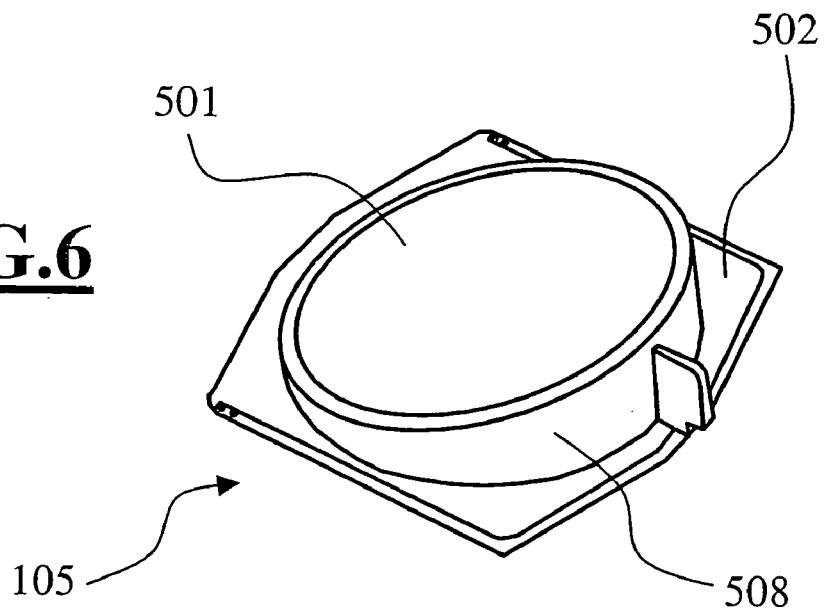
FIG. 6 is a perspective view of the cover element as seen in a second direction; and, FIG. 7 is a detail section view of the holding device with the cover element along the line VII—VII of FIG. 1.

FIGS. 5 and 6 show a cover element 105 which is suitable for insertion into a holding device of FIGS. 3 and 4.

The cover element 105 has a window section 501 for passing a viewing beam path of a surgical microscope main objective. A holding section 502 is formed on the cover element and this holding section holds the cover element 105 in the holding device explained in greater detail with respect to FIGS. 3 and 4. To prevent disturbing reflections in the viewing beam path of a surgical microscope, the window section 501 is inclined to the holding section 502 at an angle of approximately 15°. If needed, also inclination angles between 0° and 30° are advantageous in dependence upon a used surgical microscope illumination. Further, especially at an inclination angle of 15°, the cover element can be utilized for a plurality of surgical microscope illuminations.

The holding section 502 is configured to be sheet-like. The edge 503 of the holding section 502 is configured so as to be thickened and functions as a linear guide means. In this edge 503, there are notches 504 and 505 which act as detent means and coact with detents 312 and 313 of FIG. 4 of the holding device.

Figure 7:
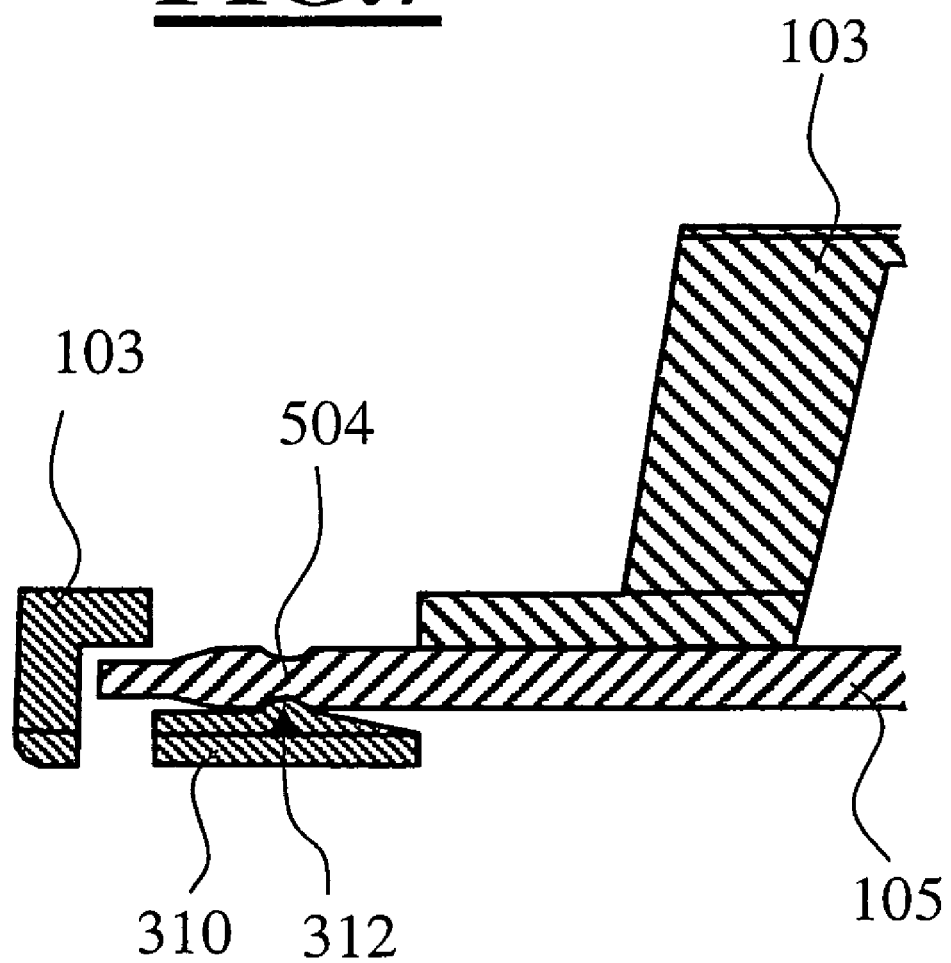

FIG. 7 shows the interaction of the notches and detents in a cover element along line VII—VII of FIG. 1. The cover element is inserted into the holding device. In the region of the notch 504 of the cover element 105, the detent 312 applies a clamping force to the cover element 105 at the longitudinal guiding bracket 310 of the holding device 103. In this way, a simultaneous latch and clamping seat is made possible when inserting the cover element 105 into the holding device 103.

As shown in FIG. 5, a handle 506 is configured on the cover element 105 and this handle facilitates the easy insertion and exchange of the cover element in the holding device for an operator. The side 507 of the holding section, which lies opposite the handle 506, has a convex contour. This convex contour of the side 507 effects a self-centering when inserting the cover element 105 into the holding device of FIG. 3 or FIG. 4 and ensures that no wedging or clamping occurs in the holding device. The form of the cover element 105 is adapted in such a manner to the drawer guide of the holding device that the cover element can be accommodated in the holding device in two orientations rotated by 180° to each other. This makes it possible to minimize disturbing reflections especially for different illuminating light configurations.

The window section 501 of the cover element is orientated inclined to the holding section 502 and is carried by a conically-shaped cylindrical window base 508. This conically-shaped configuration of the cylindrical window base makes possible a space-saving one-into-the-other stacking of several cover elements. Again, the corner regions of the cover element, as in the holding device, are configured to be rounded in order to avoid a danger of injury for the user so that the cutting open of sterile gloves can be substantially prevented.

The cover element is manufactured of plastic, for example, PMMA. Basically, the cover element could, however, also be made of quartz glass or some other transparent material.

It is understood that the foregoing description is that of the preferred embodiments of the invention and that various changes and modifications may be made thereto without departing from the spirit and scope of the invention as defined in the appended claims.

What is claimed is:

1. A holding device for attaching a drape for a surgical microscope in the region of the main objective thereof, said main objective defining an optical axis and having an outer peripheral surface and said holding device comprising:
   a holding unit having an annular side wall defining a recess for said objective; and,
   said holding unit having a plurality of individual tongue-shaped sections having respective tips and projecting from said side wall for applying a spring force onto said outer peripheral surface of said main objective when said holding unit is mounted on said main objective in order to force-tightly hold said holding unit on said main objective; and,
   said individual tongue-shaped sections projecting from said side wall into said recess inclined at an angle with respect to said optical axis in a direction away from said surgical microscope so as to permit said tips to contact engage said outer peripheral surface of said main objective to apply said spring force thereto.

2. The holding device of claim 1, said holding unit including a stop element for impacting against an end face region of said main objective.

3. The holding device of claim 1, further comprising a cover element; and, said holding unit including means for holding said cover element.

4. The holding device of claim 3, wherein said holding means includes a guide for said cover element.

5. The holding device of claim 4, wherein said holding means includes clamping means.

6. The holding device of claim 5, wherein said holding means includes latching means.

7. The holding device of claim 6, wherein said guide includes a stop section for said cover element.

8. The holding device of claim 3, wherein said cover element is matched to said holding unit so as to permit said cover element to be accommodated in said holding unit in two orientations rotated by 180° to each other.

9. The holding device of claim 1, wherein said holding unit is made of plastic.

10. The holding device of claim 1, further comprising:
    a cover element having a window section for passing a viewing beam path and/or an illuminating beam path of said surgical microscope;
    the cover element including:
    a holding section for holding said cover element in said holding unit; and,
    linear guide means in said holding section for facilitating a lateral introduction of said cover element into said holding unit.

11. The holding device of claim 10, wherein said holding section includes, at least partially, a thickened edge.

12. The holding device of claim 11, further comprising at least one notch formed in said thickened edge.

13. The holding device of claim 10, further comprising a handle formed on said cover element.

14. The holding device of claim 13, wherein said holding section defines a region lying opposite said handle and said region of said holding section has a boundary edge having a convex contour.

15. The holding device of claim 14, wherein said boundary edge has at least one rounded edge region.

16. The holding device of claim 10, further comprising a window base for carrying said window section.

17. The holding device of claim 16, wherein said window base is configured to have a conical cross section.

18. The holding device of claim 17, wherein said window section is inclined to said holding section.

19. The holding device of claim 10, said cover element being made of PMMA.

20. The holding device of claim 1, wherein said tongue-shaped sections have different lengths.

21. A holding device for attaching a drape for a surgical microscope in the region of the main objective thereof, said main objective having an outer peripheral surface and said holding device comprising:
    a holding unit defining a recess for said objective;
    said holding unit having a tongue-shaped section for applying a spring force onto said outer peripheral surface of said main objective when said holding unit is mounted on said main objective in order to force-tightly hold said holding unit on said main objective;
    said holding unit having a plurality of said tongue-shaped sections; and,
    said tongue-shaped sections having different lengths.

22. The holding device of claim 21, wherein said holding unit has an annular section defining an annular recess and said annular recess defines an axis; and, said tongue-shaped sections extend in an inclined direction to said axis.

23. The holding device of claim 22, wherein said tongue-shaped sections are directed toward the inner side of said annular section.

24. The holding device of claim 23, wherein the direction of said tongue-shaped sections to said axis is different.

25. A drape system for a surgical microscope having a main objective and said main objective defining an optical axis and having an outer peripheral surface, the drape system comprising:
    a drape;
    a holding device for attaching said drape in the region of said main objective;
    said holding device including a holding unit having an annular side wall defining a recess for said main objective;
    said holding unit having a plurality of individual tongue-shaped sections having respective tips and projecting from said side wall for applying a spring force onto said outer peripheral surface of said main objective when said holding unit is mounted on said main objective in order to force-tightly hold said holding unit on said main objective; and, said individual tongue-shaped sections projecting from said side wall into said recess inclined at an angle with respect to said optical axis in a direction away from said surgical microscope so as to permit said tips to contact engage said outer peripheral surface of said main objective to apply said spring force thereto.

26. The drape system of claim 25, said holding unit including a stop element for impacting against an end face region of said main objective.

27. The drape system of claim 25, further comprising a cover element; and, said holding unit including means for holding said cover element.

28. The drape system of claim 27, wherein said holding means includes a guide for said cover element.

29. The drape system of claim 28, wherein said holding means includes clamping means.

30. The drape system of claim 29, wherein said holding means includes latching means.

31. The drape system of claim 30, wherein said guide includes a stop section for said cover element.

32. The drape system of claim 27, wherein said cover element is matched to said holding unit so as to permit said cover element to be accommodated in said holding unit in two orientations rotated by 180° to each other.

33. The drape system of claim 25, wherein said holding unit is made of plastic.

34. A drape system for a surgical microscope having a main objective and said main objective having an outer peripheral surface, the drape system comprising:
    a drape;
    a holding device for attaching said drape in the region of said main objective;
    said holding device including a holding unit defining a recess for said main objective; and,
    said holding unit having a tongue-shaped section for applying a spring force onto said outer peripheral surface of said main objective when said holding unit is mounted on said main objective in order to force-tightly hold said holding unit on said main objective;
    said holding unit having a plurality of said tongue-shaped sections; and, said tongue-shaped sections having different lengths.

35. The drape system of claim 34, wherein said holding unit has an annular section defining an axis and defining an annular recess and said annular recess defines an axis; and, said tongue-shaped sections extend in an inclined direction to said axis.

36. The drape system of claim 35, wherein said tongue-shaped sections are directed toward the inner side of said annular section.

37. The drape system of claim 36, wherein the direction of said tongue-shaped sections to said axis is different.

38. The drape system of claim 34, said holding unit including a stop element for impacting against an end face region of said main objective.

39. The drape system of claim 34, wherein said holding unit is made of plastic.

40. The drape system of claim 34, further comprising a cover element; and, said holding unit including means for holding said cover element.

41. The drape system of claim 40, wherein said holding means includes a guide for said cover element.

42. The drape system of claim 41, wherein said holding means includes clamping means.

43. The drape system of claim 42, wherein said holding means includes latching means.

44. The drape system of claim 43, wherein said guide includes a stop section for said cover element.

45. A holding device for attaching a drape for a surgical microscope in the region of the main objective thereof, said main objective defining an optical axis and having an outer peripheral surface defining a diameter and said holding device comprising:
    a holding unit connected to said drape and having an annular wall defining a recess for said objective;
    said recess having a fixed diameter;
    said holding unit having a plurality of individual tongue-shaped sections having respective tips and projecting from said side wall for applying a spring force onto said outer peripheral surface of said main objective when said holding unit is mounted on said main objective in order to force-tightly hold said holding unit on said main objective;
    said individual tongue-shaped sections being configured to bend differently depending upon said diameter of said outer peripheral surface of said main objective to thereby hold said holding unit on said main objective independently of said fixed diameter; and,
    said individual tongue-shaped sections projecting from said side wall into said recess inclined at an angle with respect to said optical axis in a direction away from said surgical microscope so as to permit said tips to contact engage said outer peripheral surface of said main objective to apply said spring force thereto.

46. The holding device of claim 45, said holding unit including a stop element for impacting against an end face region of said main objective.

47. The holding device of claim 45, further comprising a cover element; and, said holding unit including means for holding said cover element.

48. The holding device of claim 47, wherein said holding means includes a guide for said cover element.

49. The holding device of claim 48, wherein said holding means includes clamping means.

50. The holding device of claim 49, wherein said holding means includes latching means.

51. The holding device of claim 50, wherein said guide includes a stop section for said cover element.

52. The holding device of claim 47, wherein said cover element is matched to said holding unit so as to permit said cover element to be accommodated in said holding unit in two orientations rotated by 180° to each other.

53. The holding device of claim 45 further comprising:
    a cover element having a window section for passing a viewing beam path and/or an illuminating beam path of said surgical microscope;
    the cover element including:
    a holding section for holding said cover element in said holding unit; and,
    linear guide means in said holding section for facilitating a lateral introduction of said cover element into said holding unit.

54. The holding device of claim 53, wherein said holding section includes, at least partially, a thickened edge.

55. The holding device of claim 54, further comprising at least one notch formed in said thickened edge.

56. The holding device of claim 53, further comprising a handle formed on said cover element.

57. The holding device of claim 56, wherein said holding section defines a region lying opposite said handle and said region of said holding section has a boundary edge having a convex contour.

58. The holding device of claim 57, wherein said boundary edge has at least one rounded edge region.

59. The holding device of claim 53, said cover element being made of PMMA.

60. The holding device of claim 53, further comprising a window base for carrying said window section.

61. The holding device of claim 60, wherein said window base is configured to have a conical cross section.

62. The holding device of claim 61, wherein said window section is inclined to said holding section.

* * * * *